United States Patent [19]

Davies et al.

[11] Patent Number: 4,690,562
[45] Date of Patent: Sep. 1, 1987

[54] GAS ANALYSIS APPARATUS AND METHOD

[75] Inventors: William L. Davies, Stanton St. John; Clive E. W. Hahn, Radley; Roy K. Jackson, Oxford; Thomas A. McGraghan, Fringeford; Eileen Palayiwa, Marston; Basil R. Sugg, Oxford, all of England

[73] Assignee: Penlon Limited, England

[21] Appl. No.: 746,338

[22] Filed: Jun. 19, 1985

[30] Foreign Application Priority Data

Jun. 20, 1984 [GB] United Kingdom ............... 8415670

[51] Int. Cl.⁴ ................................................ G01B 9/02
[52] U.S. Cl. ................................................. 356/361
[58] Field of Search ............................... 356/356, 361

[56] References Cited

U.S. PATENT DOCUMENTS 3,472,598 10/1969 Hossmann .
3,487,227 12/1969 Kinzly .
3,957,376 5/1976 Charsky et al. ................. 356/356
4,169,980 10/1979 Zanoni .
4,449,823 5/1984 Schwiesow .

FOREIGN PATENT DOCUMENTS 2084315A 4/1982 United Kingdom .

OTHER PUBLICATIONS

Nebe, "The Halanometer-a New Measuring Instrument for Inhalation Gas used in Anaesthesia", *Jena Review*, vol. 16, pp. 97-99, 1971.
Japanese Abstract 58-88610-Nihon Bunkou Kogyo K.K.

Primary Examiner—Davis L. Willis
Assistant Examiner—Matthew W. Koren
Attorney, Agent, or Firm—Bacon & Thomas

[57] ABSTRACT

An apparatus and method for analysing a gas of the kind adapted to produce an interference pattern displacements of which are indicative of changes of the constitution of the gas involves exposing an array 8 of photosensitive elements to the interference pattern. Respective digital indications of the intensity of the interference pattern falling of the elements are produced by means of a timing circuit 16 adapted to clock data out of the array 8 as a series of analogue pulses which are held by a fast peak detector 17 and converted by an analogue-to-digital converter 18 into digital indications. The position of a principal peak of the interference pattern is then determined by means of a microprocessor (not shown) adapted to determine the best fit of the digital indications with appropriate pre-stored values.

20 Claims, 11 Drawing Figures

FIG. 6

PERFORM CONVOLUTION OF STORED COSINE FUNCTION WITH ARRAY DATA $$\text{CORRELATION VALUE } C_i = \sum_{j=-\frac{n-1}{2}}^{\frac{n-1}{2}} S_j \, M(i+j)$$

WHERE $S_j$ = PRESTORED VALUES
$M(i+j)$ = MEASURED VALUES
$N$ = NO. OF PIXELS IN ARRAY e.g. 128
$n$ = NO. OF PIXELS IN PRESTORED PATTERN e.g. 9
AND $i$ RUNS FROM $\frac{n-1}{2}$ to $N-\frac{n-1}{2}$

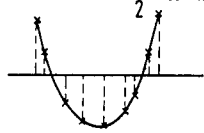

LOCATE TWO MAXIMA OF $C_i$ CORRESPONDING TO BEST FIT POSITIONS WITH MINIMA IN DATA

{ IF MAXIMUM IN $C_i$ CORRESPONDS TO TWO $i$ (i.e. TWO PIXELS), TAKE AVERAGE.

TEST FOR CORRECT ORDER OF SPACING BETWEEN MINIMA

{ SPACING BETWEEN MINIMA TYPICALLY 10 to 20 PIXELS.

ONCE MINIMA ARE IDENTIFIED, CALCULATE FROM 3 LOWEST PIXELS FOR EACH THE AVERAGE HEIGHT OF EACH MINIMUM AND CALCULATE BIAS.
$\overline{M}_p = (M_{p-1} + M_p + M_{p+1})/3$
$\overline{M}_q = (M_{q-1} + M_q + M_{q+1})/3$
$B_{pq} = \overline{M}_q - \overline{M}_p$

BIAS CORRECTION

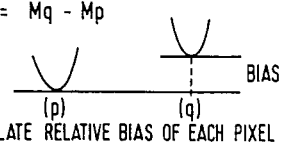

CALCULATE RELATIVE BIAS OF EACH PIXEL BETWEEN MINIMA.

$$M'_i = M_i - B_{pq} \frac{(i-p)}{(q-p)}$$

CALCULATE CENTROID OF CENTRAL PEAK BETWEEN MINIMA

SUBTRACT FROM CENTRAL PIXELS TO ZERO BASE LINE, CALCULATE CENTROID OF CENTRAL PEAK.

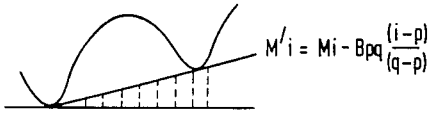

$$\overline{C} = \frac{\sum_{i=p}^{q} M'_i \cdot i}{\sum_{i=p}^{q} M'_i}$$

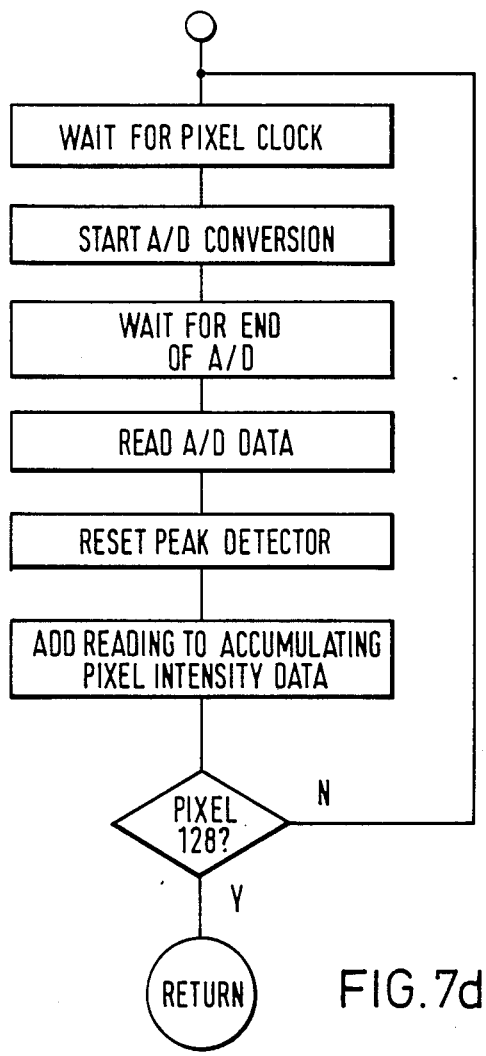

GAS ANALYSIS APPARATUS AND METHOD

This invention relates to an apparatus and method for analysing the constitution of a mixture of gases. It has particular application in the analysis of mixtures of gases and vapours used in medicine, for example in respirators and anaesthesia machines.

Many techniques are known for analysing the constitution of mixtures of gases. For example, paramagnetism, infra-red spectroscopy, ultra-violet absorption and polarography may be used for measuring the concentration of particular gases. Other techniques, such as gas chromatography, mass spectroscopy and interference refractometry have been used to measure a wide range of gases. Gas chromatography has the disadvantages that it is normally slow in action and requires high voltages which are undesirable in medical situations; mass spectrometry requires cumbersome and expensive equipment.

Prior interferometric devices involve the measurement of interference fringes and this may be done rhy manually moving a travelling microscope or the like to count fringes relative to a graticule. This procedure is time consuming and prone to errors. An automatic refractometer has been described in which the fringes fall on a pair of photocells and compensating optics are driven by a moving coil or stepper motor to move the beam. These mechanical components may wear or fail and further, it is possible for a simple device to be inconsistent in its selection of a fringe and so give a false reading.

According to the invention, there is provided a gas analyser of the kind adapted to produce an interference pattern displacements of which are indicative of changes of the constitution of the gas to be determined, comprising an array of photosensitive elements arranged to receive the interference pattern, means for providing respective digital indications of the intensity of the interference pattern falling on the elements, and digital processing means arranged to determine the best fit of the digital indications with pre-stored values so as to determine the position of at least one principal peak. By "principal peak" we mean a maximum or minimum in the intensity of the interference pattern.

The invention is applicable to interferometers of the kind employing a broad band source of light which produces an interference pattern of non-uniform shape in which it is possible to distinguish the various peaks by their shapes. The pre-stored values are selected to reflect the shape (the variation of the intensity with distance of the peak) of the chosen principal peak and by use of the best fit method it is possible to identify unambiguously a particular peak and thus measure its displacement.

The best fit is preferably determined by correlating the prestored values with a relatively small number of digital indications from successive elements starting with one particular element, and then correlating the prestored values with the same number of digital indications starting with the next element, and so on, and comparing the resulting correlation values to determine at which starting element the best fit occurs. Although the number of elements used is small relative to the total number of elements, this method is considerably more acurate than a procedure in which the minimum or maximum intensity is identified by a single measurement because a number of values are involved in the determination and so the procedure tolerates individual errors or failures in elements of the photosensitive array.

It is possible to examine the entire received interference pattern, or a limited portion thereof, such as the central maximum peak where constructive interference occurs for all wavelengths but preferably the apparatus is arranged to determine the positions of two principal peaks, preferably the minima adjacent the central maximum peak. This allows an automatic test to be performed as to the separation of the minima so as to check that it falls within an expected range.

It is possible to determine the position of the central peak from the positions of the adjacent minima by calculating the centroid or mean position of the two minima. Preferably, however, the digital indications of the intensities from all of the elements falling between the two minima are employed to determine the position of the centroid of the area of the central peak. The use of the two minima has the further advantage that "bias" errors (i.e. a gradually increasing or decreasing intensity error across the interference pattern or the output of the photosensitive array) can be compensated. In accordance with a feature of the invention the compensation is performed by calculating the average intensity value of the two minima, subtracting them to determine the amount of bias error therebetween, and using the bias error so determined to correct the intensity values of the elements of the central peak. This gives a very accurate indication of the true position of the centre of the central peak, which involves the use of a large number of the digital indications and so the process is highly insensitive to errors.

The position of the fringe pattern on the array may be determined by a simplified method of convolution, in which the prestored pattern (or template) represents a large portion of the fringe pattern, typically centered on the principal maximum and extending some way beyond the principal minima. This prestored pattern would be stored with a resolution (pixel spacing) which is typically 1 or 2 orders of magnitude finer than the resolution of the measured data. In this way the convolution would determine the position of best fit accurately to a small fraction of the pixel spacing, without the need to correct for bias or calculate the centroid of an area. (Increasing the number of points on the template means the convolution will take longer to perform. However the length of time can be minimized by performing a coarse convolution over the whole array to locate the approximate position of the pattern and then performing a fine convolution over a small area surrounding the true position. Abandoning the bias and centroid calculations would save a similar amount of time to that required for the extra convolution.)

The position of the central peak (in units of the element spacing) will be stored for comparison with a previous or subsequent fringe position to provide an indication of the displacement of the fringe pattern and hence of changes in the constitution of the gas. In order to analyse a mixture of gases the position of the interference pattern is first determined using a sample consisting purely of one constituent of the mixture, then the position is determined using a sample including the other constituent, and the displacement of the interference pattern is used to determined the concentration of the other constituent. For example, in an anaesthesia apparatus a calibration run may be performed using pure oxygen and then fresh respiratory gas consisting of a mixture of nitrous oxide and oxygen may be supplied to the gas analyser, so as to provide an indication of the concentration of nitrous oxide. In a subsequent run the concentration of an anaesthetic vapour in the respiratory gas may be determined. The relation between the displacement of the interference pattern and the concentration of a constituent of the mixture depends on the difference in the optical path lengths through the interferometer which itself depends on the refractive index of the sample and hence on its constitution. The relation may be determined empirically by the analyser using standard samples, but preferably it is calculated from a knowledge of the optical path lengths and refractive indices involved. A simple linear and additive relation may exist between the displacement and the concentration and different coefficients may be stored for calculating the concentrations of different constituents as indicated to the analyser by the operation of a manual control.

Instead of oxygen, room air might be used as the calibration reference gas. The refractive index is close to that of oxygen but the small measurement produced when oxygen is introduced during calibration serves to indicate the correct functioning of the apparatus.

In order to compensate for the various leakage currents of the photosensitive elements, the light source is preferably controllable by the processing means and digital indications of the outputs of the photosensitive elements are taken and stored as reference values with the light source turned off. The light source is then turned on and the digital intensity indications provided. The stored reference values may be subtracted from the respective intensity indications. In order to eliminate the effects of random noise, the intensity indications may be provided a number of times and the average values used.

Viewed from another aspect the invention provides a method of analysing an interference fringe pattern, comprising exposing an array of photosensitive elements to the fringe pattern, providing respective digital indications of the intensity of the interference pattern falling on the elements, and determining the best fit of the digital indications with pre-stored values so as to determine the position of the interference pattern.

An embodiment of the invention will now be described by way of example and with reference to the accompanying drawings, in which:

FIG. 6 shows the formulae used to determine the position of the interference pattern; and FIGS. 7a to 7e show the structured schematic logic of the operation of the apparatus in analysing gases in an anaesthesia machine.

Figure 1:
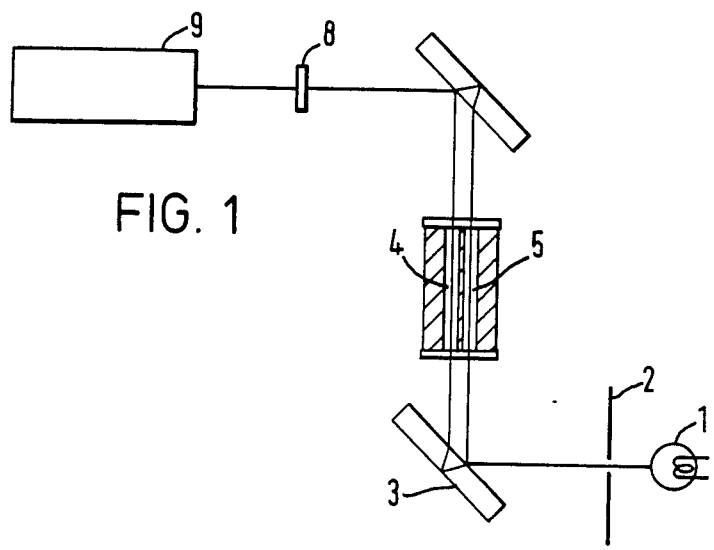
FIG. 1 is a schematic view of a gas analyser according to the invention, showing particularly the optical arrangement.
Figure 3:
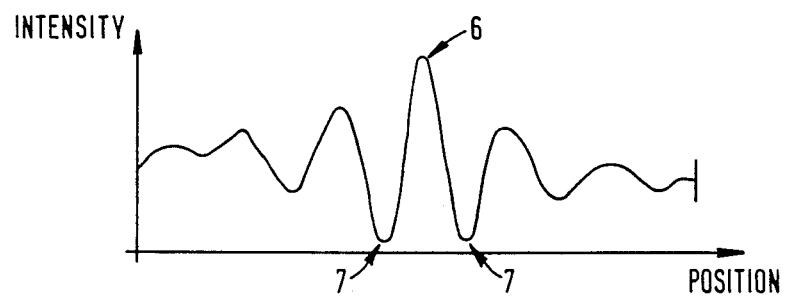
FIG. 3 illustrates a typical interference pattern obtained in the analyser of FIG. 1.

Referring to the drawings, the principles of interferometric gas analysis are illustrated in FIG. 1. The apparatus measures the difference in the optical path lengths between a reference gas and a mixture. A light source 1, such as a tungsten filament bulb, produces a beam of light through a diffuser and collimator 2 which is then split into two beams by a parallel-sided glass plate 3. One beam passes through a sample cell 4 and the other beam passes through an identical cell 5 containing a reference gas, such as oxygen or air. The light paths are then recombined and produce interference fringes. A typical fringe pattern is shown in FIG. 3: it comprises a bright central area 6 corresponding to zero path difference where the beams interfere constructively for all wavelengths. On each side of the bright area is a dark band 7 caused by destructive interference. Moving outwards there are several coloured bands where there is constructive interference for the corresponding colour components in the white light. The shift of the fringes relative to the origin obtained with the reference gas in both cells indicates the concentration of the second gas in the mixture. Both nitrous oxide and anaesthetic vapours cause a shift in the interference pattern and for concentrations in common anaesthetic practice (70% nitrous oxide, and less than 4% halothane) these are around the same order of magnitude. Thus one interferometer may be used for both gas and vapour. The shift is dependent on concentration, refractive index, pressure and temperature.

The interference pattern falls on a detector 8 consisting of an array of photosensitive elements, such as photodiodes or charge coupled devices. Each element of the array is sometimes referred to hereinafter as a "pixel". A typical array may comprise 128 photodiodes at 25 micron centres. An electronic processing circuit 9 operates to determine the position of the fringes from the outputs of the photosensitive elements, to calculate the gas concentrations and to perform other control functions as described below. The interference pattern can be adjusted by optical means so that when imaged on the array of photosensitive elements, the distance between two peaks corresponds to a sufficient number of pixels, typically 10 to 20, to provide fine resolution. The sensitivity of the instrument (i.e. deflection for unit change in concentration) is determined by the optical length of the sample cells.

Figure 2:
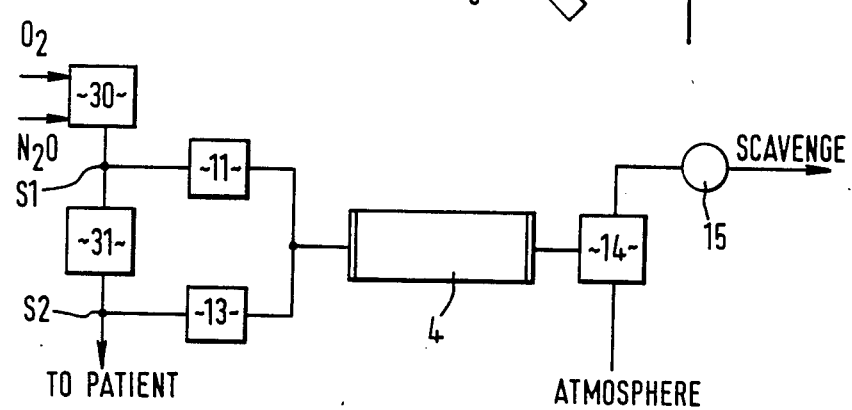
FIG. 2 shows the gas connections to the analyser of FIG. 1.

FIG. 2 shows the arrangement of gas passages for providing gases to the sample cell under the control of the electronic circuitry. An electrically controllable gas mixer 30 is connected to receive the desired gases from appropriate sources and the selected gas or mixture is supplied to a sample point S1. An anaesthetic vaporiser 31 is connected between sample point S1 and a further sample point S2. A passage from sample point $S_1$ may supply for example oxygen and nitrous oxide to the sample cell 4 via a valve 11. Similarly, a passage supplies a mixture of oxygen, nitrous oxide and anaesthetic vapour to the sample cell 4 via valve 13. Sample points S1 and S2 are located within the gas mixing system of the anaesthetic machine so that two gases (say oxygen and nitrous oxide) are mixed before flow reaches S1. Another gas or vapour is added between $S_1$ and $S_2$, before the complete mixture is passed towards the patient. In principle, the process may be extended via a further gas mixer or vaporiser to further sample points S3, S4, etc with one more component of the mixture being added between each pair of points. Valve 14 is operable selectively to connect the sample cell 4 to the suction pump 15 or to atmosphere. The valves 11, 13 and 14 and the pump 15 are under electrical control and the arrangement is such that sample gas may be drawn into the cell 4 and then equilibrated to atmospheric pressure.

Figure 4:
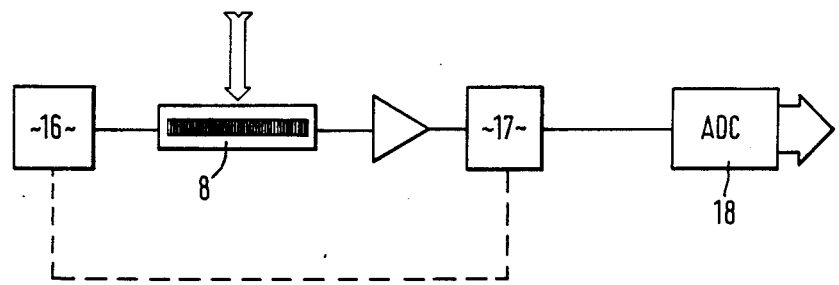
FIG. 4 is a block diagram showing the input circuitry for providing intensity values to the processing circuitry.
Figure 5:
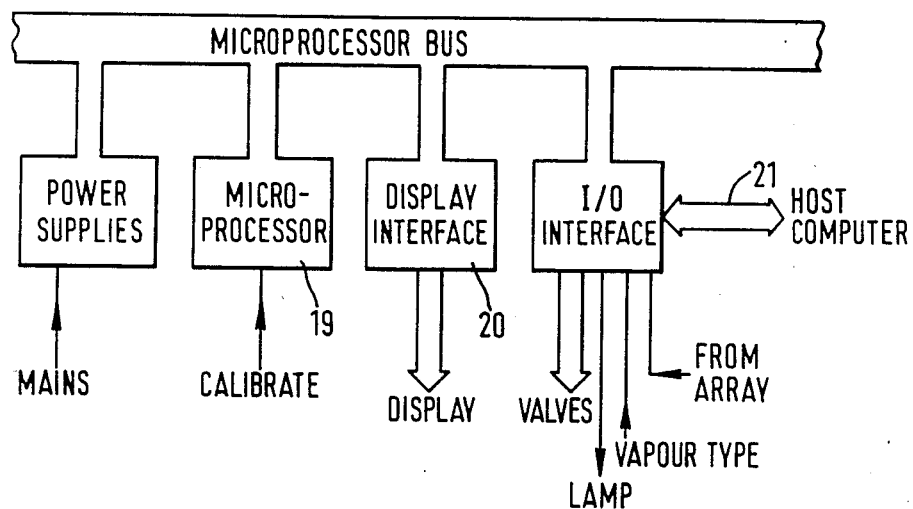
FIG. 5 is a block diagram of the processing and peripheral circuitry.

FIG. 4 shows the array 8 of photosensitive elements which are controlled by a timing circuit 16. Timing circuit 16 produces a train of 128 pulses at 150 microsecond intervals to clock data out from the array as a series of analogue pulses, the amplitude of each pulse depending on the intensity of light falling on its respective photodiode. Each pulse is amplified and held by a fast peak detector or sample and hold circuit 17 which is also controlled by the timing circuit 16. Whilst the peak value is held between the clock pulses an analogue-to-digital converter 18 converts it to a digital indication. The digital value is read into and stored by a microprocessor 19 (FIG. 5); thus the microprocessor stores a series of 128 words of bytes representing the amplitude of the light signal across the array. The results of the calculation performed by the microprocessor are displayed on a display such as a seven segment display 20 and as mentioned above the circuit controls the valves 11, 13 and 14. The microprocessor is also arranged to control the lamp 1 and connect via an interface 21 to a host computer, which may control other machine functions. Inputs to the microprocessor 19 include manual controls to indicate the vapour type in use and to indicate that a calibration mode should operate.

The microprocessor memory is pre-programmed with calibration and conversion values giving the relation between the amount of shift in the interference pattern and the concentration of various gases and vapours. It is also provided with a series of values representing the shape of the minima 7 in the interference pattern, which may resemble a cosine function. Referring to FIG. 6, the processor first operates to perform a convolution of the stored function with the array data, i.e. the digital intensity values read in to the memory. The stored values are multiplied by respective pixel intensity values for a small number of pixels, e.g. 9, starting with for example the fourth pixel, to derive a correlation value. An example of the values of a typical stored function is 27, 9, −7, −18, −23, −18, −7, 9, 27. A similar correlation value is calculated for the same number of pixels beginning with the next pixel, i.e. the nine pixels beginning with the fifth pixel, and so on. The two largest correlation values are then selected and these reveal which pixels are the starting pixels of the best fitting minima. A test in then carried out to determine the spacing in units of the pixel spacing between the two minima determined. This should agree with a design value, which might typically be between 10 and 20 pixels, as the spatial wavelength does not vary greatly. In this way it is possible to check that gross errors in the selection of the minima have not occurred. If it is found that there are two closely adjacent maximum correlation values the position of each minimum is taken to be at the average position and a third point of maximum correlation is selected as the other minimum.

A bias correction may then be carried out to compensate for uniform variations in the outputs of the photosensitive elements. The three lowest pixel intensity values are selected for each minimum and their average intensity calculated. If there is a difference between the intensities of the minima, this is an indication of the bias over the distance between them. The intensity values for the pixels between the minima, i.e. the pixels in the central peak, may then be corrected for the bias error. Finally, the centroid of the intensity values for all of the pixels in the central peak is calculated to give an indication of the true centre of the central peak. In an alternative approach, the centroid or even the midpoint of the two minima could be calculated but this may not give such an accurate indication of the true position of the fringe pattern. However, in both cases it will be seen that the use of the convolution or best fit technique described above to identify the desired fringes is effective to reduce errors and ensure that in two subsequent measurements the movement of the same fringe is determined.

Figure 7A:
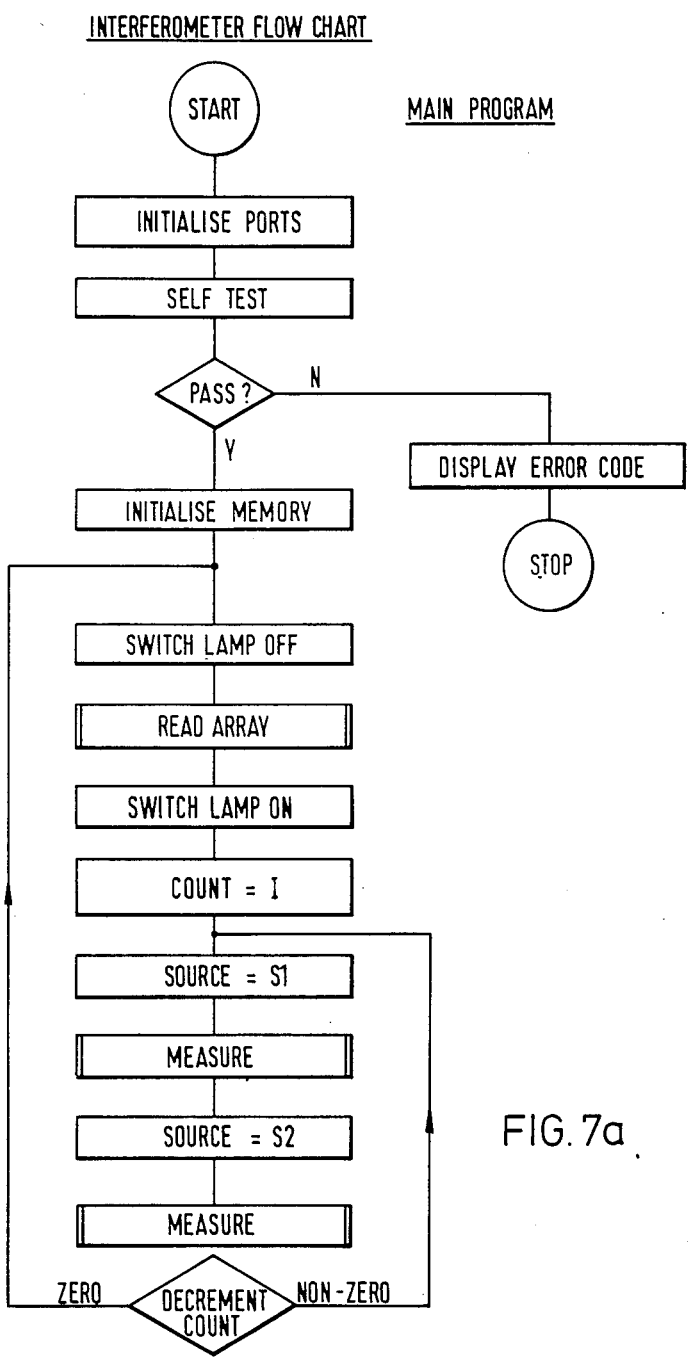
Figure 7B:
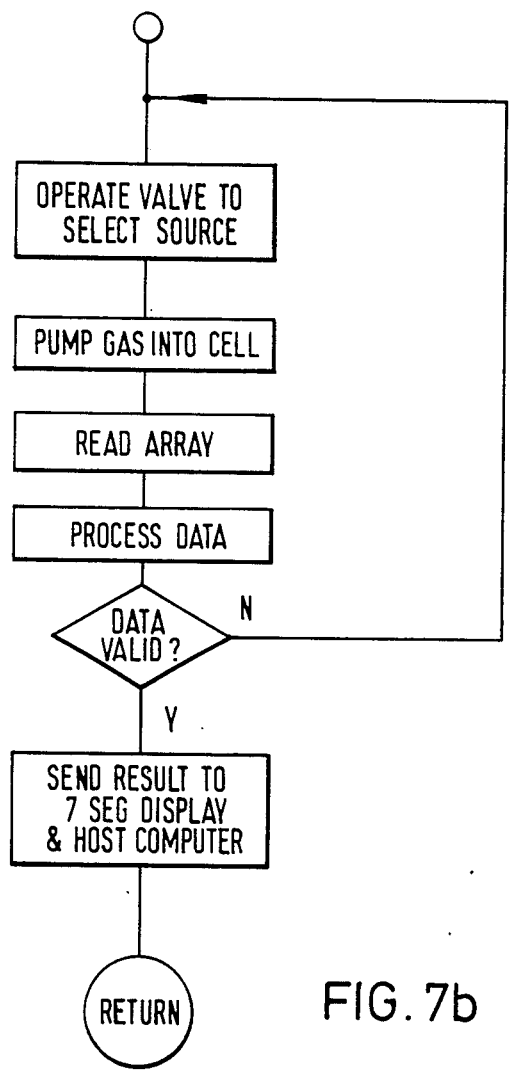
Figure 7C:
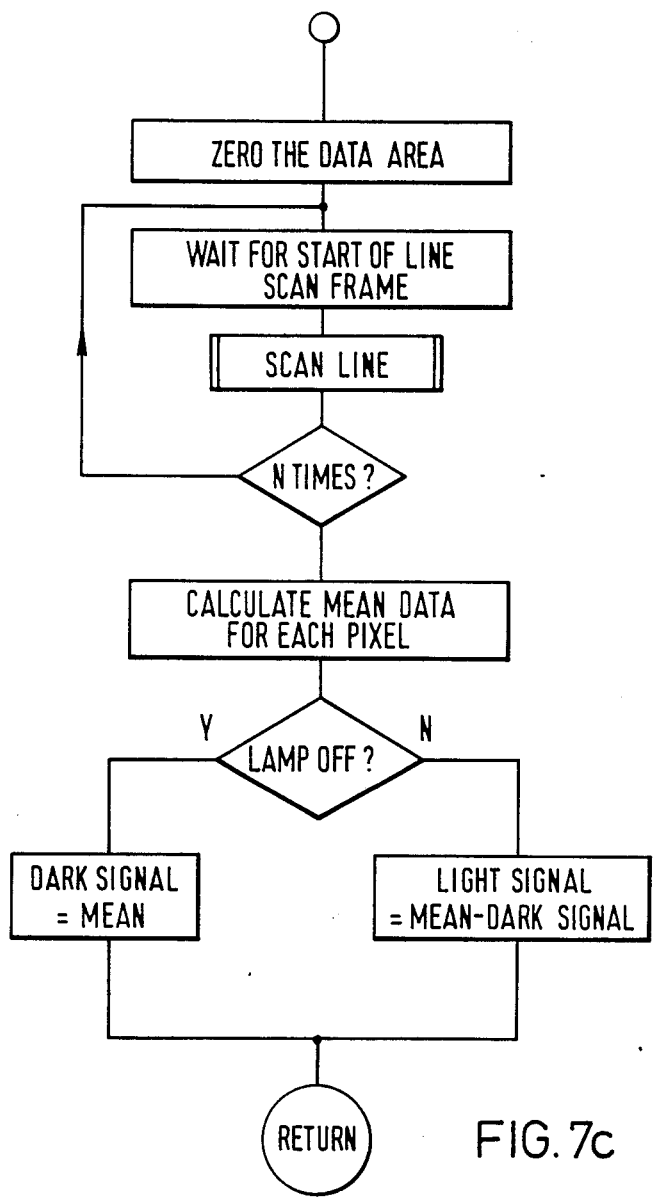
Figure 7E:
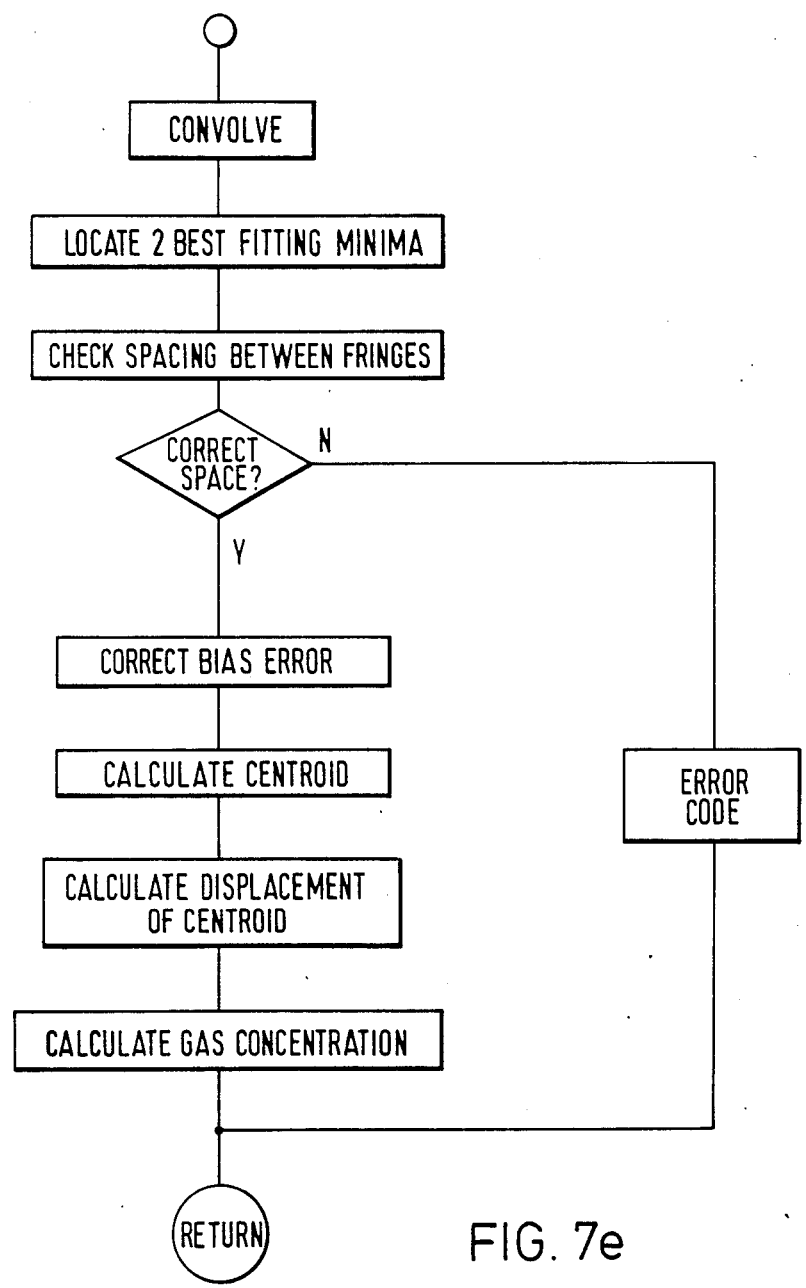

Referring to FIGS. 7a to 7e, the schematic logic of a program in the microprocessor 19 for controlling gas analysis in an anaesthesia apparatus is shown. When the mains supply is switched on various initialisation and test functions are performed. In the event of a fault, an error code is provided on the display 20 (FIG. 7a). A calibration function (not shown) may be carried out by applying 100% oxygen to the sample cell 4 and equilibrating to atmospheric pressure. The fringe position is determined as described above and the position stored. The analyser may then operate in the analysis mode in which the first gas mixture, e.g. nitrous oxide and oxygen, is pumped into the sample cell and then again equilibrated to atmospheric pressure (FIG. 7b). The fringe position is determined as follows: first of all the lamp 1 is turned off and the intensity values of the photosensitive elements read into the microprocessor memory, being indications of the leakage or dark current of the photocells (FIG. 7a,7c). The lamp is then turned on by the microprocessor and the intensity values again read. The reading of the light values is repeated a number of times and the average taken and the dark values are then subtracted to give 128 corrected values. This serves to remove the effects of random pixel and electrical noise (FIG. 7c). The position of the fringe pattern is then determined as described above with reference to FIG. 6 and the amount of fringe shift is calculated as compared to 100% oxygen (FIG. 7e). The concentrations of nitrous oxide and oxygen may then be calculated by dividing the amount of fringe shift by a prestored coefficient. The resulting value may then be displayed or used by the host computer. The valves 11, 13 and 14 and pump 15 may then be operated to draw in the nitrous oxide, oxygen and anaesthetic vapour mixture from the source S₂ and to equilibrate the pressure to atmospheric (FIG. 7a,7b), and a similar procedure to determine the fringe shift is carried out. The particular vapour in use is identified by the operator via a manual input control or by a message from the host computer and the vapour concentration is determined by dividing the amount of fringe shift as compared to the nitrous oxide and oxygen mixture by a prestored coefficient appropriate to the vapour in use. Finally, the concentration of anaesthetic vapour is displayed and sent to the host computer if required (FIG. 7b).

We claim:

1. A gas analyser which produces an interference pattern displacements of which are indicative of changes of the constitution of a gas to be determined, said analyser comprising an array of photosensitive elements arranged to receive the interference pattern, means for providing respective digital indications of the intensity of the interference pattern falling on the elements, and digital processing means arranged to determine the best fit of the digital indications with stored values so as to determine the position of at least one principal peak, wherein the best fit is determined by correlating the stored values with a number of digital indications from successive elements starting with one particular element, and then correlating the stored values with the same number of digital indications for successive elements starting with the next element, and comparing the resulting correlation values to determine at which starting element the best fit occurs.

2. A gas analyser as claimed in claim 1 which determines the positions of two minima adjacent a central maximum peak of the interference pattern.

3. A gas analyser as claimed in claim 2 wherein the digital indications of the intensities from all of the elements falling between the two minima are employed to determine the position of the centroid of the area of the central peak.

4. A gas analyzer as claimed in claim 3 which compensates for bias errors across the interference pattern or output of the photo-sensitive array by calculating the average intensity value of the two minima, subtracting them to determine the amount of bias error therebetween, and using the bias error so determined to correct the intensity values of the elements of the central peak.

5. A gas analyser as claimed in claim 1 wherein the stored values are correlated with a relatively small number of digital indications in each successive correlation.

6. A gas analyser as claimed in claim 1 wherein the stored values represent a pattern extending over a relatively large portion of the interference pattern centered on the principal maximum and extending beyond the principal minima, such pattern being stored with a resolution which is finer than the resolution of the measured data.

7. A gas analyser as claimed in claim 1 wherein the position of the principal peak is stored for comparison with a previous or subsequent peak position to provide an indication of displacement of the fringe pattern and hence of changes in the constitution of the gas.

8. A gas analyser as claimed in claim 7 for analysing a mixture of gases, wherein the position of the interference pattern is first determined using a sample consisting purely of one constituent of the mixture, then the position is determined using a sample including the other constituent, and the displacement of the interference pattern is used to determine the concentration of the other constituent.

9. A gas analyser as claimed in claim 1 wherein the light source is controllable by the processing means and digital indications of the photosensitive elements are initially taken and stored as reference values with the light source turned off, such reference values subsequently being subtracted from the respective intensity indications.

10. A method of analysing an interference fringe pattern, comprising exposing an array of photosensitive elements to the fringe pattern, providing respective digital indications of the intensity of the interference pattern falling on the elements, and determining the best fit of the digital indications with stored values so as to determine the position of the interference pattern, wherein the best fit is determined by correlating the stored values with a number of digital indications from successive elements with one particular element, and then correlating the stored values with the same number of digital indications for successive elements starting with the next element, and comparing the resulting correlation values to determine at which starting element the best fit occurs.

11. A method as claimed in claim 10 which determines the positions of two minima adjacent a central maximum peak of the interference pattern.

12. A method as claimed in claim 11 wherein the digital indications of the intensities from all of the elements falling between the two minima are employed to determine the position of the centroid of the area of the central peak.

13. A method as claimed in claim 12 which compensates for bias errors across the interference pattern or output of the photo-sensitive array by calculating the average intensity value of the two minima, subtracting them to determine the amount of bias error therebetween, and using the bias error so determined to correct the intensity values of the elements of the central peak.

14. A method as claimed in claim 10 wherein the stored values are correlated with a relatively small number of digital indications in each successive correlation.

15. A method as claimed in claim 10 wherein the stored values represent a pattern extending over a relatively large portion of the interference pattern centered on the principal maximum and extending beyond the principal minima, such prestored pattern being stored with a resolution which is finer than the resolution of the measured data.

16. A method as claimed in claim 10 wherein the interference pattern is produced by a gas analyser, displacements of the pattern being indicative of changes in constitution of a gas.

17. A method as claimed in claim 16 wherein the position of the principal peak is stored for comparison with a previous or subsequent peak position to provide an indication of displacement of the fringe pattern and hence of changes in the consitution of the gas.

18. A method as claimed in claim 17 for analysing a mixture of gases, wherein the position of the interference pattern is first determined using a sampale consisting purely of one constituent of the mixture, then the position is determined using a sample including the other constituent, and the displacement of the interference pattern is used to determine the concentration of the other constituent.

19. A method as claimed in claim 10 wherein the light source is controllable by processing means and digital indications of the photosensitive elements are initially taken and stored as reference values with the light source turned off, such reference values subsequently being subtracted from the respective intensity indications.

20. In a gas analyser for analysing the constitution of gases which comprises means for produing an interference pattern, displacements of said pattern being indicative of changes of the constitution of a gas being analysed, the improvement therein comprising:

an array of photosensitive elements arranged to receive said interference pattern, and means for providing digital indications representative of the intensity of the interference pattern falling on each respective element;

means for providing a stored pattern representing a relatively large portion of said interference pattern, such stored pattern being stored with a resolution which is finer than the resolution of the interference pattern; and processing means for determining the best fit of said digital indications from said photosensitive elements with said stored pattern whereby to determine the relative position of at least one principal peak of said interference pattern received by said array of photosensitive elements.

* * * * *